United States Patent
Wei et al.

(10) Patent No.: US 10,428,229 B2
(45) Date of Patent: Oct. 1, 2019

(54) AQUEOUS COATING MATERIAL AND METHOD FOR MANUFACTURING THE SAME

(71) Applicant: INDUSTRIAL TECHNOLOGY RESEARCH INSTITUTE, Hsinchu (TW)

(72) Inventors: Yeu-Kuen Wei, Hsinchu (TW); Shu-Yun Chien, Hsinchu (TW); Su-Mei Chen Wei, Hsinchu (TW); Yi-Che Su, Zhubei (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 60 days.

(21) Appl. No.: 15/856,475

(22) Filed: Dec. 28, 2017

(65) Prior Publication Data

US 2019/0203060 A1 Jul. 4, 2019

(51) Int. Cl.
| | | |
|---|---|---|
| *C09D 7/65* | (2018.01) | |
| *C09D 5/00* | (2006.01) | |
| *C08L 83/12* | (2006.01) | |
| *C08G 77/388* | (2006.01) | |
| *C08G 77/50* | (2006.01) | |
| *C09D 7/63* | (2018.01) | |
| *C09D 7/20* | (2018.01) | |
| *C09D 133/08* | (2006.01) | |
| *C09D 169/00* | (2006.01) | |
| *C09D 175/04* | (2006.01) | |
| *C09K 3/18* | (2006.01) | |
| *C08F 283/12* | (2006.01) | |
| *C08K 5/00* | (2006.01) | |
| *C08K 5/06* | (2006.01) | |
| *C08K 5/17* | (2006.01) | |
| *C07F 7/08* | (2006.01) | |

(52) U.S. Cl.
CPC ............. *C09D 7/63* (2018.01); *C07F 7/0878* (2013.01); *C08F 283/12* (2013.01); *C08G 77/388* (2013.01); *C08G 77/50* (2013.01); *C08K 5/0025* (2013.01); *C08K 5/06* (2013.01); *C08K 5/17* (2013.01); *C09D 5/00* (2013.01); *C09D 7/20* (2018.01); *C09D 133/08* (2013.01); *C09D 169/00* (2013.01); *C09D 175/04* (2013.01); *C09K 3/18* (2013.01)

(58) Field of Classification Search
None
See application file for complete search history.

(56) References Cited

U.S. PATENT DOCUMENTS

| | | | |
|---|---|---|---|
| 4,515,979 A | 5/1985 | Otsuki et al. | |
| 5,430,166 A | 7/1995 | Klein et al. | |
| 5,430,167 A | 7/1995 | Klein et al. | |
| 5,672,641 A | 9/1997 | Beer et al. | |
| 5,877,254 A | 3/1999 | La Casse et al. | |
| 9,487,692 B2 | 11/2016 | Nguyen et al. | |
| 2009/0117794 A1 | 5/2009 | Cheng et al. | |
| 2013/0074725 A1 | 3/2013 | Kojima et al. | |
| 2013/0157066 A1 | 6/2013 | Cheng et al. | |

FOREIGN PATENT DOCUMENTS

| | | | |
|---|---|---|---|
| CN | 101917844 A | | 12/2010 |
| CN | 103025519 A | | 4/2013 |
| CN | 103764663 A | | 4/2014 |
| CN | 105073917 A | | 11/2015 |
| EP | 0914364 B1 | | 12/2006 |
| EP | 2605904 | * | 1/2017 |
| TW | I293974 B | | 3/2008 |
| TW | I330588 B | | 9/2010 |
| TW | I370491 B | | 8/2012 |
| TW | I373476 B | | 10/2012 |
| TW | I375683 B | | 11/2012 |
| TW | I376408 B | | 11/2012 |
| TW | I433896 B | | 4/2014 |
| TW | I440674 B | | 6/2014 |
| TW | 201502131 A | | 1/2015 |
| TW | I480167 B | | 4/2015 |
| TW | I511987 B | | 12/2015 |
| TW | I570228 B | | 2/2017 |
| TW | I575035 B | | 3/2017 |
| TW | I576397 B | | 4/2017 |
| WO | WO 98/03575 A1 | | 1/1998 |

OTHER PUBLICATIONS

English abstract of CN 102417959 A, Apr. 2012, 6 pages, China.*
Chang et al., "Preparation of Water-Resistant Antifog Hard Coatings on Plastic Substrate," Langmuir, vol. 28, 2012 (Published Nov. 22, 2012), pp. 17193-17201.
Choi et al., "Superhydrophilic Coatings with Intricate Nanostructure Based on Biotic Materials for Antifogging and Antibiofouling Applications," Chemical Engineering Journal, vol. 309, 2017 (Available online Oct. 14, 2016), pp. 463-470.
Hu et al., "Highly Transparent Superhydrophilic Graphene Oxide Coating for Antifogging," Materials Letters, vol. 182, 2016 (Available online Jun. 30, 2016), pp. 372-375.
Wang et al., "Antifogging and Frost-Resisting Polyelectrolyte Coatings Capable of Healing Scratches and Restoring Transparency," Chemistry of Materials, vol. 27, 2015 (Published Nov. 10, 2015), pp. 8058-8065.

(Continued)

*Primary Examiner* — Tae H Yoon

(74) *Attorney, Agent, or Firm* — Birch, Stewart, Kolasch & Birch, LLP

(57) ABSTRACT

An aqueous coating material is provided. The aqueous coating material includes an aqueous resin and a surfactant. The surfactant having a hydrophilic segment of poly(alkylene glycol), a hydrophobic segment of siloxane, and a terminal hydrophilic group. The aqueous resin and the surfactant may have a weight ratio of 100:1 to 100:25.

17 Claims, No Drawings

(56) References Cited

OTHER PUBLICATIONS

Zhao et al., "Acrylic Coatings with Surprising Antifogging and Frost-resisting Properties," Chem. Commun., vol. 49, 2013 (Published on Oct. 24, 2013), pp. 11764-11766.

Zhao et al., "Terpolymer-based SIPN Coating with Excellent Antifogging and Frost-resisting Properties," RSC Advances, vol. 5, 2015 (Published Nov. 25, 2015), pp. 102560-102566.

Taiwanese Office Action and Search Report, dated Sep. 7, 2018, for Taiwanese Application No. 107101221.

\* cited by examiner

AQUEOUS COATING MATERIAL AND METHOD FOR MANUFACTURING THE SAME

TECHNICAL FIELD

The technical field relates to an aqueous coating material.

BACKGROUND

An anti-fog agent should satisfy certain requirements, such as providing a good anti-fog performance, being durable and easy to use, and not being harmful to humans, among others. An anti-fog agent can be a surfactant that is directly coated onto the surface of an object. In addition, the anti-fog agent can be a methacrylate-based, organic polysiloxane-based, or polyethylene glycol-based polymer film coated on the surface of the object. Silicon resin-based polymer is an economical and effective anti-fog coating material for glass and mirrors, and is used as an anti-fog agent for automotive glass. However, most of the silicon resin must be sintered at a high temperature, which is not suitable for plastic objects. The polymer film can be coated onto the surface of an object, and this method has been used for years and is widely accepted by customers. The polymer film with excellent anti-fog performance and durable property has good mechanical properties is abrasion resistant and solvent resistant. The polymer film has excellent anti-fog properties, making it especially suitable for doors, windows, freezer windows, bathroom mirrors, lenses, masks, instrument panels, automotive headlamp cover, and the like. However, the coating of the polymer film is solvent-based.

Accordingly, an aqueous, environmentally friendly, and durable anti-fog coating material is called for.

SUMMARY

One embodiment of the disclosure provides an aqueous coating material, including: an aqueous resin; and a surfactant, having a hydrophilic segment of poly(alkylene glycol), a hydrophobic segment of siloxane, and a terminal hydrophilic group.

One embodiment of the disclosure provides a method for manufacturing an aqueous coating material, including: reacting (a) hydrolyzed siloxane compound with (b1) amino crosslinker to form a surfactant, wherein the surfactant has a hydrophilic segment of poly(alkylene glycol), a hydrophobic segment of siloxane, and a terminal amino group; and mixing the surfactant with an aqueous resin to obtain an aqueous coating material.

One embodiment of the disclosure provides a method for manufacturing an aqueous coating material, including: reacting (a) hydrolyzed siloxane compound with (b2) epoxy crosslinker to form an intermediate; ring-opening the epoxy group of the intermediate to form a surfactant, wherein the surfactant has a hydrophilic segment of poly(alkylene glycol), a hydrophobic segment of siloxane, and a terminal hydroxyl group; and mixing the surfactant with an aqueous resin to obtain an aqueous coating material.

A detailed description is given in the following embodiments.

DETAILED DESCRIPTION

In the following detailed description, for purposes of explanation, numerous specific details are set forth in order to provide a thorough understanding of the disclosed embodiments. It will be apparent, however, that one or more embodiments may be practiced without these specific details.

In one embodiment of the disclosure, an aqueous coating material is provided. The aqueous coating material includes an aqueous resin and a surfactant. The surfactant has a hydrophilic segment of poly(alkylene glycol), a hydrophobic segment of siloxane, and a terminal hydrophilic group. The aqueous resin does not react with the surfactant. In some embodiments, the aqueous resin and the surfactant have a weight ratio of 100:1 to 100:25. Too little surfactant does not result in an obvious anti-fog performance of an aqueous resin coating. Too much surfactant results in a poor water resistance of the aqueous resin coating, and the aqueous resin in the coating will be dissolved by moisture and release. The surfactant has a weight average molecular weight (Mw) of 6000 to 10000. A surfactant with an Mw that is too low easily migrates out of the coating due to moisture. A surfactant with an Mw that is too high has a poor stability in the aqueous resin. In one embodiment, the surfactant is formed by reacting (a) hydrolyzed siloxane compound with (b1) amino crosslinker, and the terminal hydrophilic group in this surfactant is amino group. For example, the siloxane compound has a formula of

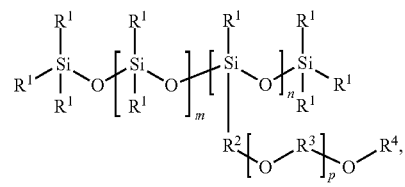

in which each of $R^1$ is independently of $C_{1-6}$ alkyl group, $R^2$ is $C_{2-10}$ alkylene group, $R^3$ is $C_{2-4}$ alkylene group, $R^4$ is H or $C_{1-4}$ alkyl group, m=0-10, n=1-10, and p=2-50. In some embodiments, the siloxane compound has a formula of

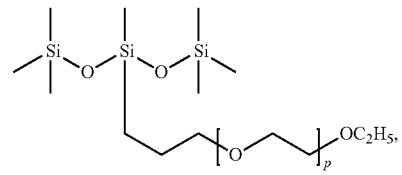

in which p is 2-10. For

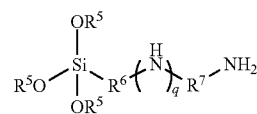

example, (b1) aminocrosslinker has a formula of Each of $R^5$ is independently of $C_{1-6}$ alkyl group, $R^6$ is $C_{1-10}$ alkylene group, $R^7$ is $C_{2-4}$ alkylene group, and q=0 or 1. In one embodiment, (b1) amino crosslinker has a formula of

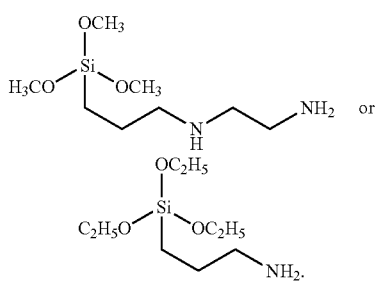

(a) Hydrolyzed siloxane compound and (b1) amino crosslinker may have a weight ratio of 100:10 to 100:200. Too little (b1) amino crosslinker results in an aqueous resin coating with insufficient water resistance. Too much (b1) amino crosslinker results in an aqueous resin coating with poor stability.

In one embodiment, the surfactant is formed by ring-opening the epoxy group of an intermediate, and the intermediate is formed by reacting (a) hydrolyzed siloxane compound with (b2) epoxy crosslinker. The terminal hydrophilic group of this surfactant is hydroxyl group. The formula of the siloxane compound is similar to that described above, and the related description is not repeated here. For example, (b2) crosslinker has a formula of

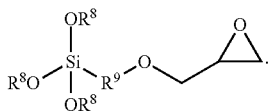

Each of $R^8$ is independently of $C_{1-6}$ alkyl group, and $R^9$ is $C_{1-10}$ alkylene group. In some embodiments, (b2) epoxy crosslinker has a formula of

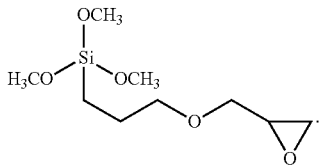 [SMILES: CO[Si](CCCOCC1CO1)(OC)OC]

(a) Hydrolyzed siloxane compound and (b2) epoxy crosslinker may have a weight ratio of 100:10 to 100:200. Too little (b2) epoxy crosslinker results in an insufficient water resistance of the aqueous resin coating. Too much (b2) epoxy crosslinker results in a poor stability of the aqueous resin coating.

In some embodiments, the aqueous resin includes polyurethane resin, carbonate resin, acrylate resin, or a combination thereof. For example, the aqueous resin may have an Mw of 10000 to 100000. An aqueous resin with an Mw that is too low cannot have a sufficient water resistance. An aqueous resin with an Mw that is too high cannot be easily used due to its viscosity that is too high.

In one embodiment, the aqueous coating material can be formed by following steps. (a) Hydrolyzed siloxane compound is reacted with (b1) amino crosslinker to form a surfactant. The siloxane compound is hydrolyzed as shown below. In the following formula, the definition of $R^1$, $R^2$, $R^3$, $R^4$, m, n, and p are similar to those defined above, and the related descriptions are not repeated here. Note that the following reaction formulae are only used to illustrate possible reaction mechanisms rather than the only reaction way. For example, some hydrolyzed siloxane compound could have two Si—OH groups rather than one Si—OH group. In addition, not only the terminal siloxane bonding but also the siloxane bondings in other positions (e.g. in the backbone) can be broken by the hydrolysis to form Si—OH. On the other hand, the hydrolysis can be performed by acid rather than alkaline.

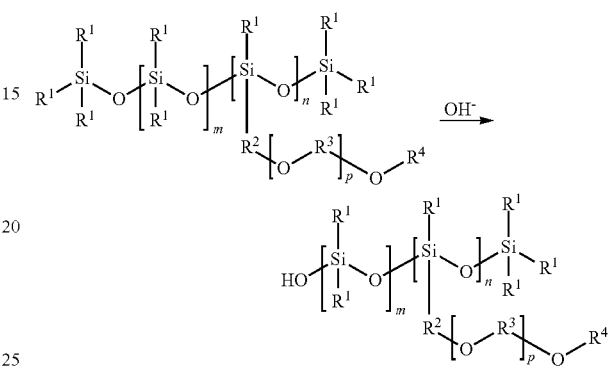

(a) Hydrolyzed siloxane compound is reacted with (b1) amino crosslinker to form a surfactant as shown below. In the following formula, the definition of $R^1$, $R^2$, $R^3$, $R^4$, $R^5$, $R^6$, $R^7$, m, n, p, and q are similar to those defined above, and the related descriptions are not repeated here. r is the polymerization degree of (b1) amino crosslinker, which can be 1 to 10. The surfactant has a hydrophilic segment of poly(alkylene glycol), a hydrophobic segment of siloxane, and a terminal amino group. (a) Hydrolyzed siloxane compound and (b1) amino crosslinker may have a weight ratio of 100:10 to 100:200. The surfactant was then mixed with the aqueous resin to form an aqueous coating material. The aqueous resin and the surfactant may have a weight ratio of 100:1 to 100:25.

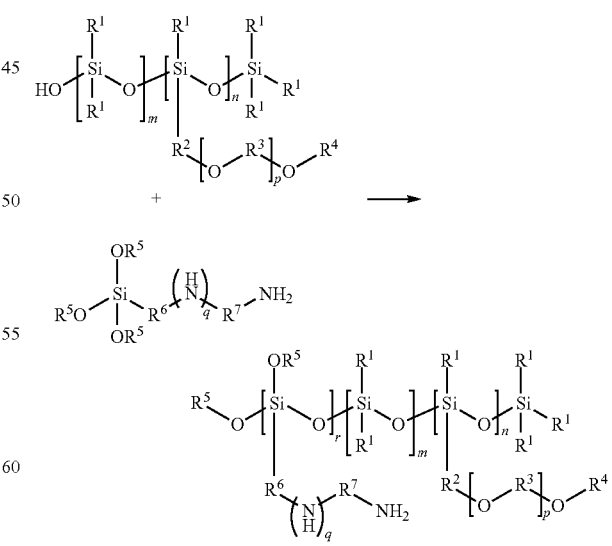

Alternatively, the aqueous coating material can be formed by reacting (a) hydrolyzed siloxane compound with (b2) epoxy crosslinker to from an intermediate as shown below.

In the following formula, the definition of $R^2, R^3, R^4, R^8, R^9$, m, n, and p are similar to those defined above, and the related descriptions are not repeated here. r is the polymerization degree of (b2) epoxy crosslinker, which can be 1 to 10.

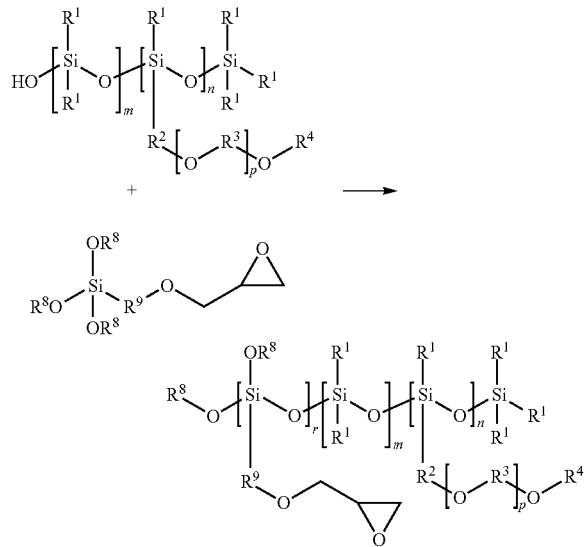

Thereafter, the epoxy group is ring-opened to form a surfactant. The surfactant has a hydrophilic segment of poly(alkylene glycol), a hydrophobic segment of siloxane, and a terminal hydroxyl group. In the following reaction formula, the epoxy group is ring-opened by acid catalyst, and the acid can be hydrochloric acid, oxalic acid, or acetic acid. However, the epoxy group can be ring-opened by an alkaline catalyst in another embodiment. The alkaline can be a general alkaline such as sodium hydroxide. (a) Hydrolyzed siloxane compound and (b2) epoxy crosslinker may have a weight ratio of 100:10 to 100:200. The surfactant is then mixed with the aqueous resin to form an aqueous coating material. The aqueous resin and the surfactant may have a weight ratio of 100:1 to 100:25.

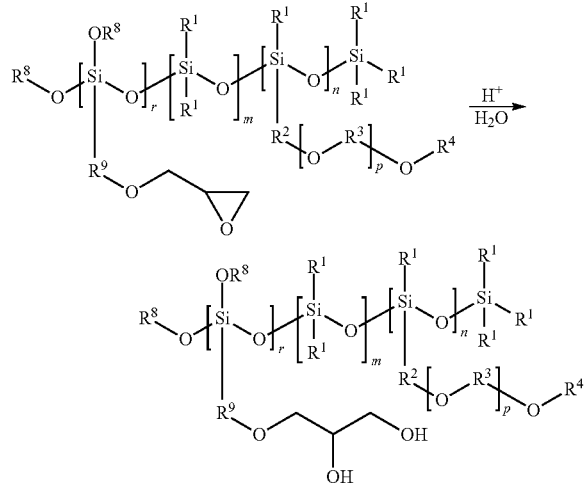

The aqueous coating material can be coated onto a substrate (e.g. lens) and then baked to be dried, thereby forming an anti-fog coating to protect the substrate. Note that the surfactant and the aqueous resin have hydrogen bondings therebetween. The surfactant does not easily release due to the interaction of the hydrogen bondings. Since the interaction of the hydrogen bondings is a reversible balance, the surfactant may migrate to the coating surface to recover its anti-fog performance even if the coating surface is consumed. As proven in experiments, the anti-fog coating has properties such as wash resistance, wipe resistance, high temperature moisture resistance, long-acting period, and the like.

Below, exemplary embodiments will be described in detail so as to be easily realized by a person having ordinary knowledge in the art. The inventive concept may be embodied in various forms without being limited to the exemplary embodiments set forth herein. Descriptions of well-known parts are omitted for clarity, and like reference numerals refer to like elements throughout.

EXAMPLES

Example 1-1

Siloxane compound (Dow Corning super-wetting agent) and 10 wt % NaOH solution were mixed. The mixture stood for several days to be hydrolyzed. The hydrolyzed mixture was filtered to collect the filtrate, thereby obtaining hydrolyzed siloxane compound. The filtrate, isopropyl alcohol, and water were evenly mixed, and amino crosslinker N-(2-aminoethyl)-3-aminopropyltrimethoxysilane (AEAPTES, Aldrich) was slowly added into the mixture to be continuously stirred at room temperature for 5 hours. The amino crosslinker and the hydrolyzed siloxane compound were reacted to form a surfactant. The amounts of the hydrolyzed siloxane compound, isopropyl alcohol, water, and the amino crosslinker and the appearance of the surfactant solution are tabulated in Table 1.

Example 1-2

Example 1-2 was similar to Example 1-1, and the difference in Example 1-2 was the amounts of the hydrolyzed siloxane compound, isopropyl alcohol, water, and the amino crosslinker. The amounts of the hydrolyzed siloxane compound, isopropyl alcohol, water, and the amino crosslinker and the appearance of the surfactant solution in Example 1-2 are tabulated in Table 1.

Example 1-3

Example 1-3 was similar to Example 1-1, and the difference in Example 1-3 was the amounts of the hydrolyzed siloxane compound, isopropyl alcohol, water, and the amino crosslinker. The amounts of the hydrolyzed siloxane compound, isopropyl alcohol, water, and the amino crosslinker and the appearance of the surfactant solution in Example 1-3 are tabulated in Table 1.

The hydrolysis of the siloxane compound in Examples 1-1 to 1-3 is shown below, in which p is 1 to 10.

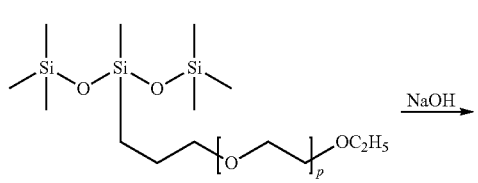

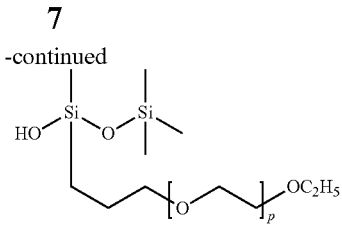

In Examples 1-1 to 1-3, the hydrolyzed siloxane compound and the amino crosslinker are reacted as shown below.

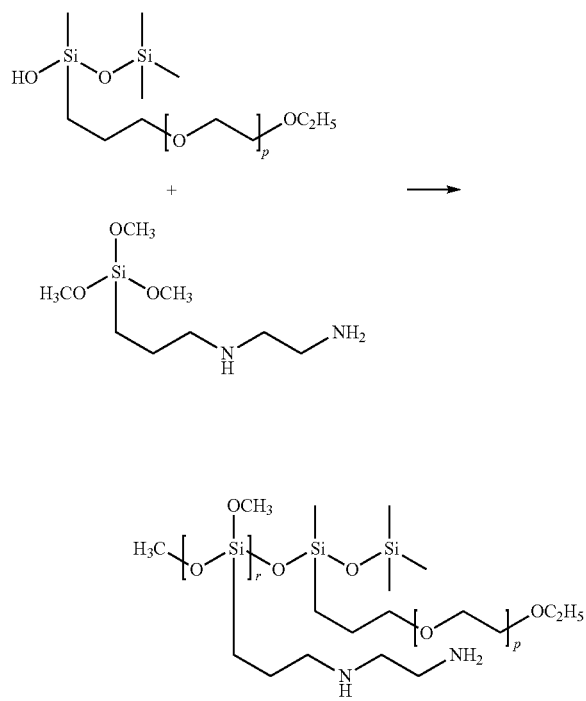

Note that the above reaction formulae are only used to illustrate possible reaction mechanisms rather than the only reaction way. For example, some hydrolyzed siloxane compound could have two Si—OH groups rather than one Si—OH group. In addition, the r in the above formula means the polymerization degree of the amino crosslinker, and r may be 1 to 5.

TABLE 1

(The unit is gram)

|  | Example | | |
|---|---|---|---|
|  | 1-1 | 1-2 | 1-3 |
| Amino crosslinker | 10 | 20 | 30 |
| Hydrolyzed siloxane compound | 90 | 120 | 120 |
| Isopropyl alcohol | 200 | 268.8 | 268.81 |
| Water | 2000 | 2688.0 | 2688.01 |
| Appearance of the surfactant solution | Clear liquid, pale yellow | Clear liquid, yellow | Clear liquid, deep yellow |

Example 2-1

The surfactant solution in Example 1-2 was slowly added into aqueous polyurethane resin (AnFong UN-3011) to form an aqueous coating material. The amounts of the surfactant and the aqueous polyurethane resin are tabulated in Table 2.

Example 2-2

Example 2-2 was similar to Example 2-1, and the difference in Example 2-2 was the amount of the surfactant. The amounts of the surfactant and the aqueous polyurethane resin in Example 2-2 are tabulated in Table 2.

Example 2-3

Example 2-3 was similar to Example 2-1, and the difference in Example 2-3 was the amount of the surfactant. The amounts of the surfactant and the aqueous polyurethane resin in Example 2-3 are tabulated in Table 2.

TABLE 2

(The unit is gram)

|  | Example | | |
|---|---|---|---|
|  | 2-1 | 2-2 | 2-3 |
| Aqueous polyurethane resin | 100 | 100 | 100 |
| Surfactant | 4 | 8 | 16 |

The aqueous coating material (in Examples 2-1 to 2-3) was coated onto a transparent carbonate resin sheet, and then baked to be dried at 120° C. to form a sample of a coating on the sheet. The sample was dipped in water for 96 hours to check whether the coating being peeled from the sheet (Soaked in water test).

50° C. water was put into a container. The opening of the container was covered by the sample with the coating face down, thereby measuring the period of forming fog on the sample surface. If the period of forming fog was longer than or equal to 30 seconds, the coating would be regarded as to pass the 50° C. water vapor anti-fog test (ASTM F659). It means that the coating had the anti-fog performance.

The soaked in water test and the anti-fog test results of the samples in Examples 2-1 to 2-3 are tabulated in Table 3.

TABLE 3

| Aqueous coating material | 2-1 | 2-2 | 2-3 |
|---|---|---|---|
| Soaked in water test | Pass | Pass | Pass |
| 50° C. water vapor anti-fog test | Pass | Pass | Pass |

Example 3-1

The siloxane compound (Dow Corning super-wetting agent) and 10 wt % NaOH solution were mixed. The mixture stood for several days to be hydrolyzed. The hydrolyzed mixture was filtered to collect the filtrate, thereby obtaining hydrolyzed siloxane compound. The filtrate, isopropyl alcohol, and water were evenly mixed, and epoxy crosslinker (Aldrich, Glymo) was slowly added into the mixture to be continuously stirred at room temperature for 8 hours. The epoxy crosslinker and the hydrolyzed siloxane compound were reacted to form an intermediate. 1N HCl was added to the intermediate to ring-open the epoxy group of the intermediate, thereby obtaining a surfactant. The amounts of the hydrolyzed siloxane compound, isopropyl alcohol, water, the epoxy crosslinker, and HCl and the appearance of the surfactant solution are tabulated in Table 4.

Example 3-2

Example 3-2 was similar to Example 3-1, and the difference in Example 3-2 was the amounts of the hydrolyzed siloxane compound and the epoxy crosslinker. The amounts of the hydrolyzed siloxane compound, isopropyl alcohol, water, the epoxy crosslinker, and HCl and the appearance of the surfactant solution in Example 3-2 are tabulated in Table 4. In Example 3-2, the siloxane compound before being hydrolyzed by NaOH had an Mw of 600 to 1000, the hydrolyzed siloxane compound had an Mw of 1000 to 1200, the intermediate had an Mw of 6000 to 10000, and the surfactant had an Mw of 6000 to 10000. The Mw values of the substances were measured by gel permeation chromatography (GPC). In addition, the intermediate had an IR signal of 910 cm$^{-1}$ (epoxy group). The surfactant had an IR signal of 840 cm$^{-1}$ and a weaken IR signal of 910 cm$^{-1}$, it means that the epoxy group of the intermediate was ring-opened to form the surfactant.

Example 3-3

Example 3-3 was similar to Example 3-1, and the difference in Example 3-3 was the amounts of the hydrolyzed siloxane compound and the epoxy crosslinker. The amounts of the hydrolyzed siloxane compound, isopropyl alcohol, water, the epoxy crosslinker, and HCl and the appearance of the surfactant solution in Example 3-3 are tabulated in Table 4.

The hydrolysis of the siloxane compound in Examples 3-1 to 3-3 is shown below, in which p is 1 to 10.

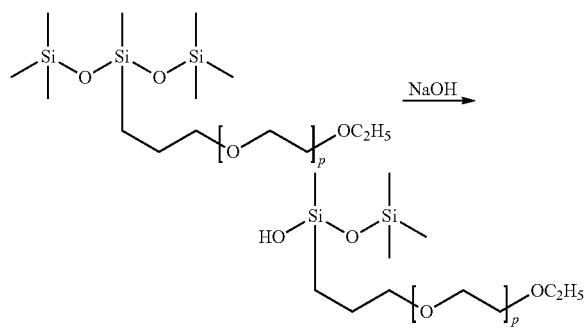

In Examples 3-1 to 3-3, the hydrolyzed siloxane compound and the epoxy crosslinker are reacted to form the intermediate as shown below.

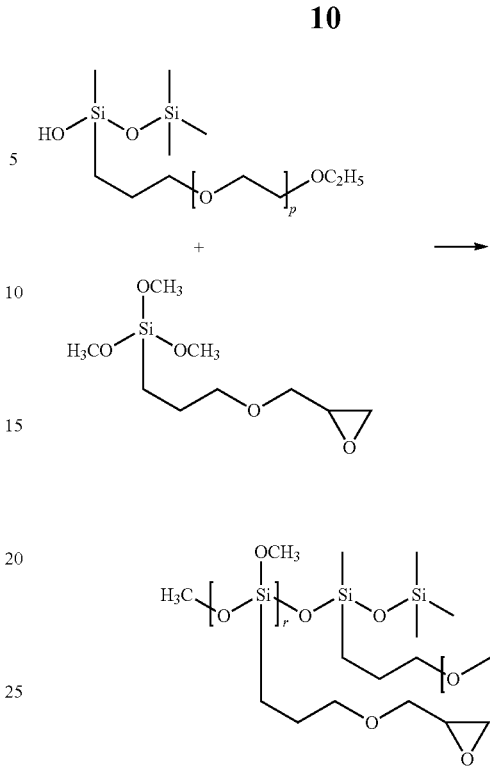

In Examples 3-1 to 3-3, the epoxy group of the intermediate was ring-opened by the acid catalyst to form the surfactant as shown below.

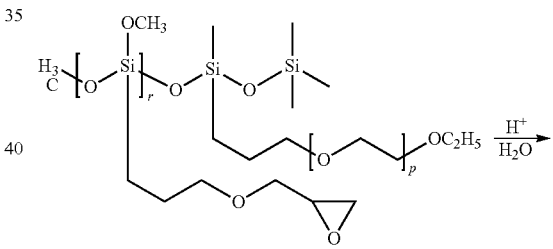

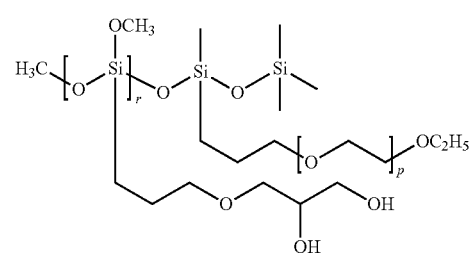

Note that the above reaction formulae are only used to illustrate possible reaction mechanisms rather than the only reaction way. For example, some hydrolyzed siloxane compound could have two Si—OH groups rather than one Si—OH group. In addition, the r in the above formula means the polymerization degree of the epoxy crosslinker, and r may be 1 to 5.

TABLE 4

| (The unit is gram) | | | |
|---|---|---|---|
| | Example | | |
| | 3-1 | 3-2 | 3-3 |
| Epoxy crosslinker | 90 | 75 | 60 |
| Hydrolyzed siloxane compound | 60 | 75 | 90 |
| Isopropyl alcohol | 250 | 250 | 250 |
| Water | 2500 | 2500 | 2500 |
| 1N HCl | 50 | 50 | 50 |
| Appearance of the surfactant solution | Clear liquid | Clear liquid | Clear liquid |

Example 4-1

The surfactant solution in Example 3-2 was slowly added into a mixture of first aqueous polyurethane resin (AnFong UN-3011) and second aqueous polyurethane resin (AnFong CUD-4835) to form an aqueous coating material. The amounts of the surfactant, the first aqueous polyurethane resin, and the second aqueous polyurethane resin are tabulated in Table 5.

Example 4-2

Example 4-2 was similar to Example 4-1, and the difference in Example 4-2 was the amount of the surfactant. The amounts of the surfactant, the first aqueous polyurethane resin, and the second aqueous polyurethane resin in Example 4-2 are tabulated in Table 5. The aqueous coating material had a viscosity of about 80 cps at room temperature. The aqueous coating material after being in storage at room temperature for 1 month had a viscosity of about 100 cps at room temperature. Accordingly, the surfactant was only mixed with the aqueous polyurethane resins, rather than reacted with the aqueous polyurethane resins.

Example 4-3

Example 4-3 was similar to Example 4-1, and the difference in Example 4-3 was the amount of the surfactant. The amounts of the surfactant, the first aqueous polyurethane resin, and the second aqueous polyurethane resin in Example 4-2 are tabulated in Table 5.

TABLE 5

| (The unit is gram) | | | |
|---|---|---|---|
| | Example | | |
| | 4-1 | 4-2 | 4-3 |
| First aqueous polyurethane resin | 50 | 50 | 50 |
| Second aqueous polyurethane resin | 50 | 50 | 50 |
| Surfactant | 4 | 8 | 16 |

The aqueous coating material (in Examples 4-1 to 4-3) was coated onto a transparent carbonate resin sheet, and then baked to be dried at 120° C. to form a sample of a coating on the sheet. The sample was tested by the soaked in water test, the anti-fog test, and a wipe test, and the test results are tabulated in Table 6.

The wipe test was performed by following steps. 80° C. water was put into a beaker, and the beaker was covered by the sample with the coating-sidedown. The sample was taken from the beaker, and the coating was wiped by a dry cloth, and then put back on the beaker. The above action was repeated every 10 seconds until the coating lost its anti-fog performance. The beaker was disposed on a heat-preserving device or a heating device to ensure the water temperature in the beaker be kept at 80° C. . If the coating could be wiped more than or equal to 10 times, the coating would be regarded as to pass the wipe test.

TABLE 6

| Aqueous coating material | 4-1 | 4-2 | 4-3 |
|---|---|---|---|
| Soaked in water test | Pass | Pass | Pass |
| 50° C. water vapor anti-fog test | Pass | Pass | Pass |
| Wipe test | Pass | Pass | Pass |

Comparative Example 1

The intermediate in Example 3-2 (not ring-opened by acid) is slowly added into the mixture of the first aqueous polyurethane resin (AnFong UN-3011) and the second aqueous polyurethane resin (AnFong CUD-4835) to form an aqueous coating material. The amount of the intermediate in Comparative Example 1 was equal to the amount of the surfactant in Example 4-2, and the amounts of the first aqueous polyurethane resin and the second aqueous polyurethane resin were similar to those in Example 4-2. The aqueous coating material had a viscosity of about 80 cps at room temperature. The aqueous coating material after being in storage at room temperature for 1 month had a viscosity of about 1000 cps at room temperature. Accordingly, if the intermediate (not being ring-opened) was directly mixed with the aqueous polyurethane resins, the aqueous polyurethane resins would react with the epoxy groups of the intermediate, thereby dramatically increasing the viscosity of the aqueous coating material.

On the other hand, the aqueous coating material of Comparative Example 1 was coated onto a transparent carbonate resin sheet, and then baked to be dried at 120° C. to form a sample of a coating on the sheet. The sample was tested by the wipe test as described above. However, the sample lost its anti-fog performance after being wiped 3 to 5 times. It means that the coating did not pass the wipe test.

Comparative Example 2

The solvent-based coating material VPP (FSI company) was coated onto a transparent carbonate resin sheet, and then baked to be dried at 120° C. to form a sample of a coating on the sheet. The sample was tested by the wipe test as described above. However, the sample lost its anti-fog performance after being wiped 3 to 5 times. It means that the coating did not pass the wipe test.

Comparative Example 3

The solvent-based coating material AF332 (NCS company) was coated onto a transparent carbonate resin sheet, and then baked to be dried at 120° C. to form a sample of a coating on the sheet. The sample was tested by the wipe test as described above. However, the sample lost its anti-fog performance after being wiped only 5 times. It means that the coating did not pass the wipe test. The sample was tested by the anti-fog test as described above. However, it did not pass the anti-fog test, which means that the coating had a poor anti-fog performance.

It will be apparent to those skilled in the art that various modifications and variations can be made to the disclosed methods and materials. It is intended that the specification and examples be considered as exemplary only, with the true scope of the disclosure being indicated by the following claims and their equivalents.

What is claimed is:

1. An aqueous coating material, comprising:
   an aqueous resin; and
   a surfactant, having a hydrophilic segment of poly(alkylene glycol), a hydrophobic segment of siloxane, and a terminal hydrophilic group,
   wherein the surfactant is formed by reacting (a) hydrolyzed siloxane compound with (b1) amino crosslinker, and the terminal hydrophilic group is amino group,
   wherein the siloxane compound has a chemical formula:

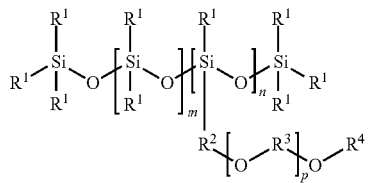

wherein each of $R^1$ is independently of $C_{1-6}$ alkyl group,
   $R^2$ is $C_{2-10}$ alkylene group,
   $R^3$ is $C_{2-4}$ alkylene group,
   $R^4$ is H or $C_{1-4}$ alkyl group,
   m=0-10,
   n=1-10, and
   =2-50;
   wherein (b1) amino crosslinker has a chemical formula:

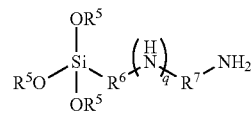

wherein each of $R^5$ is independently of $C_{1-6}$ alkyl group,
   $R^6$ is $C_{1-10}$ alkylene group,
   $R^7$ is $C_{2-4}$ alkylene group, and
   q=0 or 1.

2. The aqueous coating material as claimed in claim 1, wherein the aqueous resin and the surfactant have a weight ratio of 100:1 to 100:25.

3. The aqueous coating material as claimed in claim 1, wherein (a) hydrolyzed siloxane compound and (b1) amino crosslinker have a weight ratio of 100:10 to 100:200.

4. The aqueous coating material as claimed in claim 1, wherein the aqueous resin comprises polyurethane resin, carbonate resin, acrylic resin, or a combination thereof.

5. An aqueous coating material, comprising:
   an aqueous resin; and
   a surfactant, having a hydrophilic segment of poly(alkylene glycol), a hydrophobic segment of siloxane, and a terminal hydrophilic group,
   wherein the surfactant is formed by ring-opening an epoxy group of an intermediate, in which the intermediate is formed by reacting (a) hydrolyzed siloxane compound with (b2) epoxy crosslinker, and the terminal hydrophilic group is hydroxyl group,
   wherein the siloxane compound has a chemical formula:

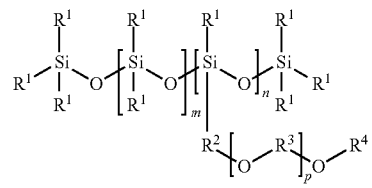

wherein each of $R^1$ is independently of $C_{1-6}$ alkyl group,
   $R^2$ is $C_{2-10}$ alkylene group,
   $R^3$ is $C_{2-4}$ alkylene group,
   $R^4$ is H or $C_{1-4}$ alkyl group,
   m=0-10,
   n=1-10, and
   =2-50;
   wherein (b2) epoxy crosslinker has a chemical formula:

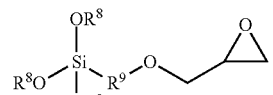

wherein each of $R^8$ is independently of $C_{1-6}$ alkyl group, and
   $R^9$ is $C_{1-10}$ alkylene group.

6. The aqueous coating material as claimed in claim 5, wherein (a) hydrolyzed siloxane compound and (b2) epoxy crosslinker have a weight ratio of 100:10 to 100:200.

7. The aqueous coating material as claimed in claim 5, wherein the aqueous resin and the surfactant have a weight ratio of 100:1 to 100:25.

8. The aqueous coating material as claimed in claim 5, wherein the aqueous resin comprises polyurethane resin, carbonate resin, acrylic resin, or a combination thereof.

9. A method for manufacturing an aqueous coating material, comprising:
   reacting (a) hydrolyzed siloxane compound with (b1) amino crosslinker to form a surfactant, wherein the surfactant has a hydrophilic segment of poly(alkylene glycol), a hydrophobic segment of siloxane, and a terminal amino group; and
   mixing the surfactant with an aqueous resin to obtain an aqueous coating material.

10. The method as claimed in claim 9, wherein the aqueous resin and the surfactant have a weight ratio of 100:1 to 100:25.

11. The method as claimed in claim 9, wherein the siloxane compound has a chemical formula:

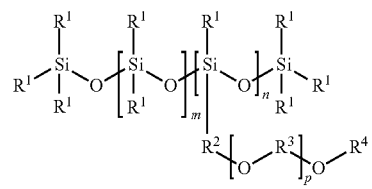

wherein each of RI is independently of $C_{1-6}$ alkyl group,
$R^2$ is $C_{2-10}$ alkylene group,
$R^3$ is $C_{2-4}$ alkylene group,
$R^4$ is H or $C_{1-4}$ alkyl group,
m=0-10,
n=1-10, and
p=2-50;
wherein (b1) amino crosslinker has a chemical formula:

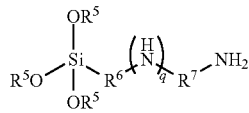

wherein each of $R^5$ is independently of $C_{1-6}$ alkyl group,
$R^6$ is $C_{1-10}$ alkylene group,
$R^7$ is $C_{2-4}$ alkylene group, and
q=0 or 1.

12. The method as claimed in claim 9, wherein (a) hydrolyzed siloxane compound and (b1) amino crosslinker have a weight ratio of 100:10 to 100:200.

13. The method as claimed in claim 9, wherein the aqueous resin comprises polyurethane resin, carbonate resin, acrylic resin, or a combination thereof.

14. A method for manufacturing an aqueous coating material, comprising:
    reacting (a) hydrolyzed siloxane compound with (b2) epoxy crosslinker to form an intermediate;
    ring-opening the epoxy group of the intermediate to form a surfactant, wherein the surfactant has a hydrophilic segment of poly(alkylene glycol), a hydrophobic segment of siloxane, and a terminal hydroxyl group; and
    mixing the surfactant with an aqueous resin to obtain an aqueous coating material, wherein the siloxane compound has a chemical formula:

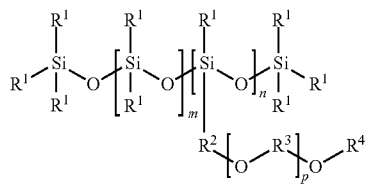

wherein each of RI is independently of $C_{1-6}$ alkyl group,
$R^2$ is $C_{2-10}$ alkylene group,
$R^3$ is $C_{2-4}$ alkylene group,
$R^4$ is H or $C_{1-4}$ alkyl group,
m=0-10,
n=1-10, and
p=2-50;
wherein (b2) epoxy crosslinker has a chemical formula:

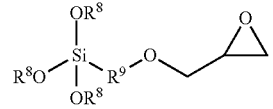

wherein each of $R^8$ is independently of $C_{1-6}$ alkyl group, and $R^9$ is Clio alkylene group.

15. The method as claimed in claim 14, wherein the aqueous resin and the surfactant have a weight ratio of 100:1 to 100:25.

16. The method as claimed in claim 14, wherein (a) hydrolyzed siloxane compound and (b2) epoxy crosslinker have a weight ratio of 100:10 to 100:200.

17. The method as claimed in claim 14, wherein the aqueous resin comprises polyurethane resin, carbonate resin, acrylic resin, or a combination thereof.

* * * * *